United States Patent [19]

Marhold et al.

[11] 4,436,941
[45] Mar. 13, 1984

[54] PROCESS FOR THE ISOMERIZATION OF ALKYLBENZOTRIFLUORIDES

[75] Inventors: Albrecht Marhold, Leverkusen; Erich Klauke, Odenthal, both of Fed. Rep. of Germany

[73] Assignee: Bayer Aktiengesellschaft, Leverkusen, Fed. Rep. of Germany

[21] Appl. No.: 449,331

[22] Filed: Dec. 13, 1982

[30] Foreign Application Priority Data

Dec. 24, 1981 [DE]  Fed. Rep. of Germany ....... 3151364

[51] Int. Cl.³ ............................................. C07C 17/24
[52] U.S. Cl. ..................................... 570/144; 570/151
[58] Field of Search ................................ 570/144, 151

[56] References Cited

U.S. PATENT DOCUMENTS 3,553,274 1/1971 Lewis et al. ......................... 570/151
3,560,579 2/1971 Bacha .
3,577,470 12/1968 Bacha .

Primary Examiner—Charles F. Warren
Assistant Examiner—Joseph A. Boska
Attorney, Agent, or Firm—Sprung, Horn, Kramer & Woods

[57] ABSTRACT

Alkylbenzotrifluorides can be isomerized in the presence of hydrogen fluoride.

20 Claims, No Drawings

PROCESS FOR THE ISOMERIZATION OF ALKYLBENZOTRIFLUORIDES

This invention relates to a process for the isomerization and subsequent isolation of alkylbenzotrifluorides.

The preparation of alkylbenzotrifluorides by alkylation of benzotrifluoride generally produces a mixture of isomers, which consists principally of the para- and meta-isomers. As a rule, it is necessary for the further processing of the benzotrifluorides, for example to give trifluoromethylbenzyl chlorides (U.S. Pat. No. 3,465,051) to employ the pure isomers. The latter can be obtained by distillation of the mixture of isomers. In this procedure, there always results as a by-product an undesired proportion of the isomer which is not required and which cannot be processed to give the desired end product.

Thus, the object of the invention is to isolate one isomer virtually exclusively from a mixture of isomers of alkylbenzotrifluorides prepared in a manner in itself known, in which process no loss and no unavoidable attack on the other isomer occurs.

For this purpose, a process for the isomerization of benzotrifluorides which are substituted by at least one alkyl group has been found, which is characterized in that the alkylbenzotrifluoride is treated with hydrogen fluoride.

Optionally the alkylbenzotrifluorides are substituted preferably by one fluoro-, chloro-, or bromo-radical.

Apart from mixtures of isomers, it is obviously also possible in the process according to the invention to employ a pure isomer and to convert it into another.

By the process according to the invention, a monoalkylbenzotrifluoride is preferentially obtained as meta- and para-isomers and a dialkylbenzotrifluoride is preferentially obtained as the syn- and asyn-isomers.

The alkyl radicals in the alkylbenzotrifluorides are preferably lower, straight-chain or branched hydrocarbon radicals (lower alkyl) having 1 to, say, 6 carbon atoms. Examples which may be mentioned are methyl, ethyl, propyl, isopropyl, butyl, isobutyl, pentyl, isopentyl, hexyl and isohexyl.

Alkylbenzotrifluorides according to the present invention contain one or more alkyl groups. However, monoalkyl- and dialkylbenzotrifluorides are preferably employed for the process according to the invention.

The most favourable range of temperature for the isomerization according to the invention depends on the particular compound and the isomer which is desired to be formed. In general, the isomerization is carried out in the temperature range from 0° to 200° C., preferably from 10° to 150° C.

Generally speaking, the choice of a lower temperature favours the formation of the para- or asym-isomers and the higher temperature favours the formation of the meta- or sym-isomers.

The isomerization of methylbenzotrifluoride, for example, is preferably carried out in the temperature range from 100° to 150° C.

When the isomerisation according to the invention is carried out at higher temperatures, the process is advantageously carried out under pressure, preferably in an autoclave under the inherent (autogenous) pressure of the system. In general, the process according to the invention is carried out at a pressure in the range from about 1 to 150 bar.

The position of the isomer equilibrium can also be changed by the choice of the pressure. In general, a higher pressure favours the formation of the meta- or sym-isomers and a lower pressure favours the formation of the para- or asym-isomers.

Working under pressure increases the solubility of the hydrogen fluoride in the alkylbenzotrifluoride and thus also increases the rate of isomerization.

The amount of hydrogen fluoride employed for the isomerization can be within a very wide range. Since, due to the low solubility of the alkylbenzotrifluoride in hydrogen fluoride, the process according to the invention is generally carried out in a two-phase system, the rate of isomerization is determined, inter alia, by the degree of mixing of the two phases. Thus, in order to achieve a rate of isomerization adequate for industrial purposes, a minimum amount of hydrogen fluoride is advantageous. This advantageous minimum amount of largely depends on the technical requirements.

The upper limit of the amount of hydrogen fluoride largely depends only on the economic advantages and it is not limited for the process according to the invention.

In general, the process according to the invention is carried out with an amount of 0.5 to 20 mols, preferably 2 to 10 mols of hydrogen fluoride, relative to 1 mol of alkylbenzotrifluoride.

When hydrogen fluoride is used in excess, it is employed as a solvent or diluent.

Obviously, it is also possible to carry out the process according to the invention in the presence of other solvents or diluents. Suitable solvents or diluents for this purpose are those which are not changed under the conditions according to the invention and, if appropriate, increase the miscibility of the components. The following solvents or diluents may be mentioned as examples: trichlorofluoromethane, 1,1,2-trichloro-1,2,2-trifluoroethane, 1,1,1-trifluoro-2,2-dichloroethane, 1,3-bistrifluoromethylbenzene and 3-nitrobenzotrifluoride.

The process according to the invention can also be carried out in the gas phase. For this purpose, the components are passed through a reaction tube which optionally contains packing material.

It is possible to carry out the process according to the invention discontinuously or continuously.

The process according to the invention is carried out, for example, as follows: The reactants are mixed in any desired sequence and heated to the isomerization temperature, if appropriate, in the presence of a solvent or diluent and, if desired, under increased pressure. The setting up of the equilibrium can be detected with the aid of analytical methods, for example by GC analysis. The components are then separated from one another. The undesired component, where it is still present in relatively large amounts, are subjected again to the isomerisation according to the invention and thus, if appropriate after several repetitions, virtually exclusively only one alkylbenzotrifluoride isomer is obtained.

The separation of the components is generally carried out by distillation. In this process, the hydrogen fluoride is initially separated off and this can be employed again for further isomerization.

In particular, using a continuous procedure, only the desired isomer is separated off and the residue is recycled to the process according to the invention.

Obviously, there are numerous processes known for isomerizing alkylated aromatic compounds (C. C. Price, Org. Reactions 3, 1-82 (1946) G. A. Olah, Friedel Crafts and Related Reactions, volume II, Interscience Publ., New York 1964).

The catalysts used for this purpose are compounds which have Friedel-Crafts activity and are also employed for alkylations of aromatic compounds. By these processes, for example, the isomeric xylenes can be converted one into another.

However, this method of isomerization fails when, in addition to the alkyl group, other substituents are present which themselves can take part in Friedel-Crafts reactions. For this reason, no methods are known which can be used to isomerize alkylbenzotrifluorides. This is because the trifluoromethyl group in the benzotrifluoride reacts by self-condensation with the Friedel-Crafts catalysts to give resinous products (J. Am. Chem. Soc. 1938, 60, 1,697 and Bull. Soc. Chem. France 1962, 587). No isomerization was to be expected with the resinous products.

The pure alkylbenzotrifluoride isomers are intermediate products for anilines, which are of interest, for example, for dyestuffs or plant protection agents (British Pat. No. 2,027,699 and German Offenlegungsschrift No. 2,750,170).

EXAMPLE 1

200 ml of anhydrous hydrogen fluoride were initially introduced into a VA stainless steel autoclave and 100 g of a mixture of 3-isopropylbenzotrifluoride (78%) and 4-isopropylbenzotrifluoride (22%) were added. The pressure in the autoclave was increased to 3 bar by pumping in nitrogen. The reaction mixture was then heated at 60° C. for 3 hours. After cooling down and distilling off the hydrogen fluoride, the ratio of isopropylbenzotrifluoride isomers was determined by gas chromatographic analysis. There are 91% by weight of 3-isopropylbenzotrifluoride and 9% of 4-isopropylbenzotrifluoride.

EXAMPLE 2

A mixture of 100 ml of hydrogen fluoride and 80 g of 3-isopropylbenzotrifluoride was initially introduced into a VA stainless steel autoclave. The pressure in the autoclave was increased to 10 bar by pumping in nitrogen. The reaction mixture was then stirred at 15° C. for 6 hours. The analysis by gas chromatography showed a composition of 21.2% of 4-isopropylbenzotrifluoride and 78.8% by weight of 3-isopropylbenzotrifluoride.

EXAMPLE 3

50 ml of hydrogen fluoride and 50 g of 3,5-diisopropylbenzotrifluoride were stirred at 15° C. under atmospheric pressure for 5 hours. Analysis by gas chromatography showed a proportion of 3.5% of 2,5-diisopropylbenzotrifluoride together with 96% of starting material.

EXAMPLE 4

On repeating Example 3 under a pressure of nitrogen of 10 bar, the proportion of 2,5-diisopropylbenzotrifluoride rose to 9.1%.

EXAMPLE 5

On repeating Example 4 under a pressure of 10 bar and with an increase in the ratio of hydrogen fluoride to 3,5-diisopropylbenzotrifluoride to 4:1, the proportion of 2,5-diisopropylbenzotrifluoride rose to 11.8% by weight.

EXAMPLE 6

A mixture of 30 ml of hydrogen fluoride and 50 g of 2,5-diisopropylbenzotrifluoride is stirred at 60° C. under a pressure of nitrogen of 8 bar for 3 hours. Analysis by gas chromatography shows a ratio of 87.8% by weight of starting material to 12.2% by weight of 3,5-diisopropylbenzotrifluoride.

EXAMPLE 7

A mixture of 50 ml of hydrogen fluoride and 50 g of 2-methylbenzotrifluoride was heated at 120° C. for 5 hours, the hydrogen fluoride was distilled off and the organic material was subjected to steam distillation. Analysis by gas chromatography showed a proportion of 3.5% of 3-methylbenzotrifluoride in 95.9% of 2-methylbenzotrifluoride.

EXAMPLE 8

A mixture of 30 ml of hydrogen fluoride and 50 g of 2-methyl-5-bromobenzotrifluoride is heated at 140° C. under a pressure of nitrogen of 28 bar for 5 hours. After cooling down, the organic phase was analysed. 7.2% by weight of 3-methyl-5-bromobenzotrifluoride had been obtained by isomerization.

EXAMPLE 9

A mixture of 50 ml of hydrogen fluoride and 18 g of 3,4-dimethylbenzotrifluoride is heated at 125° C. under a pressure of nitrogen of 25 bar for 5 hours. Analysis by gas chromatography after distillation of the reaction mixture showed the following distribution: 64.2% by weight of starting material, 24.9% by weight of 3,5-dimethylbenzotrifluoride and 10.9% by weight of 2,5-dimethylbenzotrifluoride.

EXAMPLE 10 (Comparison Example)

100 g of 2-methylbenzotrifluoride were initially introduced at 20° C. and 10 g of boron trifluoride were passed in. Resinification to high-molecular weight compounds occurred immediately. No isomerization product could be isolated from this.

What is claimed is:

1. A process for isomerizing an alkylbenzotrifluoride which comprises contacting said alkylbenzotrifluoride with hydrogen fluoride.
2. A process according to claim 1, wherein the process is carried out at a temperature of 0° to 200° C.
3. A process according to claim 1, wherein the process is carried out at a pressure from 1 to 150 bar.
4. A process according to claim 2, wherein the process is carried out at a pressure in the range of 1 to 150 bar.
5. A process according to claim 1, wherein 2 to 10 mols of hydrogen fluoride are employed per mol of alkylbenzotrifluoride.
6. A process according to claim 1, wherein the process is carried out in the liquid phase.
7. A process according to claim 1, wherein the process is carried out in the gas phase.
8. A process according to claim 1, wherein the alkylbenzotrifluoride is one in which the alkyl group contains 1 to 6 carbon atoms in the chain.
9. A process according to claim 1, wherein the process is carried out at a temperature of 10° to 150° C.
10. A process according to claim 1, wherein the process is carried out at a temperature of 100° to 150° C.

and the alkyl benzotrifluoride is a methyl benzotrifluoride.

11. A process according to claim 1, wherein the process is carried out employing 0.5 to 20 mols of hydrogen fluoride per mol of alkyl benzotrifluoride.

12. A process according to claim 1, wherein a mixture of alkylbenzotrifluoride is treated with hydrogen fluoride.

13. A process according to claim 1, wherein the alkylbenzotrifluoride is a polyalkyl benzotrifluoride.

14. A process according to claim 1, wherein 3,5-diisopropylbenzotrifluoride is contacted with hydrogen fluoride.

15. A process according to claim 1, wherein 2,5-diisopropylbenzotrifluoride is contacted with hydrogen fluoride.

16. A process for isomerizing an alkylbenzotrifluoride which comprises contacting said alkylbenzotrifluoride with hydrogen fluoride wherein said alkylbenzotrifluoride contains a fluoro, chloro or bromo group on the ring.

17. A process according to claim 1, wherein 2-methyl-5-bromobenzotrifluoride is contacted with hydrogen fluoride.

18. A process according to claim 1, wherein 3,4-dimethylbenzotrifluoride is contacted with hydrogen fluoride.

19. A process according to claim 1, wherein 2-methylbenzotrifluoride is contacted with hydrogen fluoride.

20. A process according to claim 1, wherein a mixture of 3-isopropylbenzotrifluoride and 4-isopropylbenzotrifluoride are treated with hydrogen fluoride.

* * * * *